US012624204B2

(12) United States Patent
Davidson et al.

(10) Patent No.: US 12,624,204 B2
(45) **Date of Patent: *May 12, 2026**

(54) ULTRA-HIGH MOLECULAR WEIGHT POLYMERS AND METHODS OF USING THE SAME

(71) Applicant: University of Florida Research Foundation, Inc., Gainesville, FL (US)

(72) Inventors: Cullen L. Davidson, Gainesville, FL (US); Wallace G. Sawyer, Gainesville, FL (US); Brent S. Sumerlin, Gainesville, FL (US); Juan M. Urueña Vargas, Gainesville, FL (US)

(73) Assignee: University of Florida Research Foundation, INC., Gainesville, FL (US)

( * ) Notice: Subject to any disclaimer, the term of this patent is extended or adjusted under 35 U.S.C. 154(b) by 741 days.

This patent is subject to a terminal disclaimer.

(21) Appl. No.: 17/898,545

(22) Filed: Aug. 30, 2022

(65) Prior Publication Data

US 2023/0076717 A1 Mar. 9, 2023

Related U.S. Application Data

(60) Provisional application No. 63/239,027, filed on Aug. 31, 2021.

(51) Int. Cl.

| | |
|---|---|
| *C08L 33/24* | (2006.01) |
| *A61K 9/00* | (2006.01) |
| *A61K 47/54* | (2017.01) |
| *A61K 47/69* | (2017.01) |
| *C08F 220/54* | (2006.01) |
| *C08L 43/00* | (2006.01) |
| *C08L 53/00* | (2006.01) |

(52) U.S. Cl.

CPC .............. *C08L 33/24* (2013.01); *A61K 9/006* (2013.01); *A61K 47/54* (2017.08); *A61K 47/542* (2017.08); *A61K 47/6903* (2017.08); *C08F 220/54* (2013.01); *C08L 43/00* (2013.01); *C08L 53/00* (2013.01)

(58) Field of Classification Search

CPC .......... C08L 33/24; C08L 43/00; C08L 53/00; C08F 220/54; A61K 9/006; A61K 47/54; A61K 47/542; A61K 47/6903

See application file for complete search history.

(56) References Cited

U.S. PATENT DOCUMENTS

| | | | | |
|---|---|---|---|---|
| 7,832,856 | B2 | 11/2010 | Vanderbilt et al. | |
| 7,988,988 | B2 | 8/2011 | Valint, Jr. et al. | |
| 8,071,121 | B2 | 12/2011 | Chauhan et al. | |
| 8,410,190 | B2 | 4/2013 | Zhu et al. | |
| 8,534,031 | B2 | 9/2013 | Mcgee et al. | |
| 9,464,300 | B2 | 10/2016 | Prieve et al. | |
| 2010/0162663 | A1 | 7/2010 | Mcgee et al. | |
| 2015/0094255 | A1 * | 4/2015 | Ribbeck .................. | A61P 31/00 514/21.3 |

FOREIGN PATENT DOCUMENTS

| | | | |
|---|---|---|---|
| EP | 1236068 | B1 | 8/2008 |
| RU | 2745207 | C2 | 3/2021 |
| WO | 2021145249 | A1 | 7/2021 |

OTHER PUBLICATIONS

Odian, G., Principles of Polymerization, Third Edition, John Wiley & Sons, Inc., 1991, pp. 19-24.*

ISR Mailed Jan. 23, 2023; International Patent Application PCT/US22/75616 Filed Aug. 30, 2022.

RU Office Action issued in RU Application No. 2024101716.

Alamelu Mahalingam et al: "Inhibition of the transport of HIV using a pH responsive synthetic mucin-like polymer system", Biomaterials, Elsevier, Amsterdam, NL, vol. 32, No. 33, May 1, 2011 8343-8355, DOI: 10.1016/J.BIOMATERIALS.2011.05.001.

Huang Kui et al: "Synthesis and Characterisation of Self-Assembling Block Copolymers Containing Bioadhesive End Groups",Macromolecules, American Chemical Society, US, vol. 3, No. 2, Mar. 11, 2002, pp. 397-406, DOI: 10.1021/BM015650P.

Prüfert Felix et al: "Enhancing the efficiency of thiomers: Utilizing a highly mucoadhesive polymer as backbone for thiolation and preactivation", European Journal of Pharmaceutical Sciences, Elsevier Amsterdam, NL, vol. 96, Oct. 1, 2016 (Oct. 1, 2016), pp. 309-315, DOI: 10.1016/J.EJPS.2016.09.031.

EP Office Action Received May 22, 2025 for 22865714.4.

* cited by examiner

*Primary Examiner* — Patrick D Niland

(74) *Attorney, Agent, or Firm* — Thomas | Horstemeyer LLP.

(57) ABSTRACT

The present disclosure provides for compositions including at least one type of water-soluble polymer, methods of making the water-soluble polymer, structures having the water-soluble polymer disposed thereof, and methods of use thereof.

26 Claims, 1 Drawing Sheet

Table 1

| HGNC ID | symbol | *membrane associated* | epithelium:location | |
|---|---|---|---|---|
| 23282 | MUC20 | | conjunctiva | cornea |
| 7508 | MUC1 | | conjunctiva | cornea |
| 7514 | MUC4 | | conjunctiva | cornea |
| 15582 | MUC16 | | conjunctiva | cornea |
| 7512 | MUC2 | gel forming | conjunctiva | |
| 7515 | MUC5AC | gel forming | conjunctiva | |
| 7516 | MUC5B | gel forming | lacrimal gland | |
| 7518 | MUC7 | soluble | lacrimal gland | | tear film (rows 7508–7515)

*secretory*

ULTRA-HIGH MOLECULAR WEIGHT POLYMERS AND METHODS OF USING THE SAME

CROSS-REFERENCE TO RELATED APPLICATIONS

This application claims the benefit of and priority to U.S. Provisional Application Ser. No. 63/239,027, having the title "ULTRA-HIGH MOLECULAR WEIGHT POLYMERS AND METHODS OF USING THE SAME" filed Aug. 31, 2021, the disclosure of which is incorporated herein in by reference in its entirety.

BACKGROUND

The eye's first line of defense against the external environment is a thin stratified layer of moist epithelial cells at the surface of the cornea which are shielded by an aqueous and mucinous tear film. Ocular health, durability, and comfort are inexorably linked to the ability of these epithelial cells to produce mucins to form the glycocalyx and stabilize the tear film. Ocular mucins contribute to homeostasis on the ocular surface, maintain clarity of the cornea and the tear film, and provide a physical barrier of protection against foreign debris (e.g., pathogens, toxins, and particles) while permitting the rapid passage of selected gases, fluids, ions, and nutrients.

The cornea and conjunctiva express lower molecular weight membrane-spanning mucins (MUC1, MUC4, MUC16, and MUC20), which anchor the secretory and gel-forming mucins (MUC2, MUC5AC) produced by goblet cells found in the conjunctival epithelia. The mucins present in the tear film (MUC1, MUC2, MUC4, MUC5AC, and MUC16) together form a gel layer that serves to maintain hydration and clarity of the ocular surface, provide lubrication, and resist adhesion between the corneal and conjunctival epithelia during an eyeblink.

These mucins create a gel-spanning hydrogel network, called the glycocalyx, which stabilizes the tear film and prevents dewetting. This gel network is primarily crosslinked through physical crosslinks, as opposed to chemical crosslinks. Critically, the weak physical crosslinks and the large mesh-size of mucin gels result in a surface with an intrinsically low shear stress during sliding and a low yield stress. The physical crosslinks break and heal dynamically under conditions when the yield stress is exceeded (e.g., during blinking); the gel spanning mucin network acts like a mechanical fuse limiting the potentially damaging level of stress that can be transmitted to the underlying epithelial cells.

Table 1 (FIG. 1) shows a list of the mucins found in the ocular environment. This wide array of mucins function as a system to create a gel spanning network with finite yield stress, shear thinning, and maintain a smooth and uniform film thickness across the optical interface. Gel-forming and soluble mucins are not formed by corneal epithelial cells.

The eyes are rarely at rest during waking hours and blink about 20,000 times in a day. During a blink, the eyelid wiper accelerates to a maximum speed of approximately 100 mm/s, approaches the lower eyelid, and then retracts back; the entire process takes place in ~100 milliseconds. The contact pressure exerted on the cornea by the eyelid during this activity has not been directly measured but is thought to be on the order of 1-5 kPa.

A schematic of the corneal epithelium, tear film, mucins associated with the ocular surface, including mucin MUC20 secreted between cells, and the waxy lipid layer is shown schematically in the inset of FIG. 2. The homeostasis in the healthy eye is a dynamic equilibrium that requires low shear stress across the cornea and conjunctiva. This achieved through the maintenance of a tear film comprised of mucins, salts, proteins, and a complex array of cytokines, chemokines, and growth factors. Defects in the composition of the tear film can lead to elevated levels dehydration and shear stress. Both tissues are highly innervated with pain receptors and shear stresses above physiologically "normal" level can produce the perception of pain. The tear film (~5 μm thickness) covers the corneal epithelial cells of the ocular surface (~55 μm thickness). The lipid rafts (50-100 nm in thickness) are produced by meibomian glands at the rim of the eyelids and are thought to impede evaporation of the tear film and prevent fine dust and debris from entering the ocular environment. The inset also illustrates the large molecular weight and complex structure of secretory and gel-forming mucins, as well as soluble, tear film mucins. The ultrastructure of the corneal epithelium and detail of the microvilli on the surface of the stratified squamous epithelium increase the surface area for secreting membrane-bound mucins MUC1, MUC4, and MUC16. Together these mucins anchor the secretory and soluble mucins and form a bio-polymer hydrogel, called the glycocalyx, which stabilizes the tear film and prevents dewetting. Dry eye discomfort may have an underlying etiology that involves frictional shear stresses exceeding physiological levels that can be well tolerated. The quality of the tear film is critically important for both of these applications.

SUMMARY

The present disclosure provides for compositions including at least one type of water-soluble polymer, methods of making the water-soluble polymer, structures having the water-soluble polymer disposed thereof, and methods of use thereof.

The present disclosure provides for a composition comprising: a first water-soluble polymer having a molecular weight of about 10 kDa to 10,000 kDa, wherein the first water-soluble polymer includes a plurality of backbone units and at least one first type of a mucin-binding unit, wherein the backbone units comprise greater than 50% of the first water-soluble polymer based on molecular weight, wherein the first type of mucin-binding unit comprises of 1 unit up to 50% of the first water-soluble polymer based on molecular weight, wherein the first type of mucin-binding unit is functionalized so the water-soluble polymer has the characteristic of altering the hydration, rheology, or both of a mucin polymer, a second water-soluble polymer, or a combination thereof, wherein altering the hydration, rheology, or both is achieved through mucoadhesion, mucolability, mucointegration, or a combination thereof.

The present disclosure provides for a synthetic method of making the first water-soluble polymer described above and herein, comprising: polymerizing a backbone unit and at least one mucin-binding unit to form the first water-soluble polymer described above and herein.

BRIEF DESCRIPTION OF THE DRAWINGS

Further aspects of the present disclosure will be more readily appreciated upon review of the detailed description of its various embodiments, described below, when taken in conjunction with the accompanying drawings.

DETAILED DESCRIPTION

Figures 1, 2:
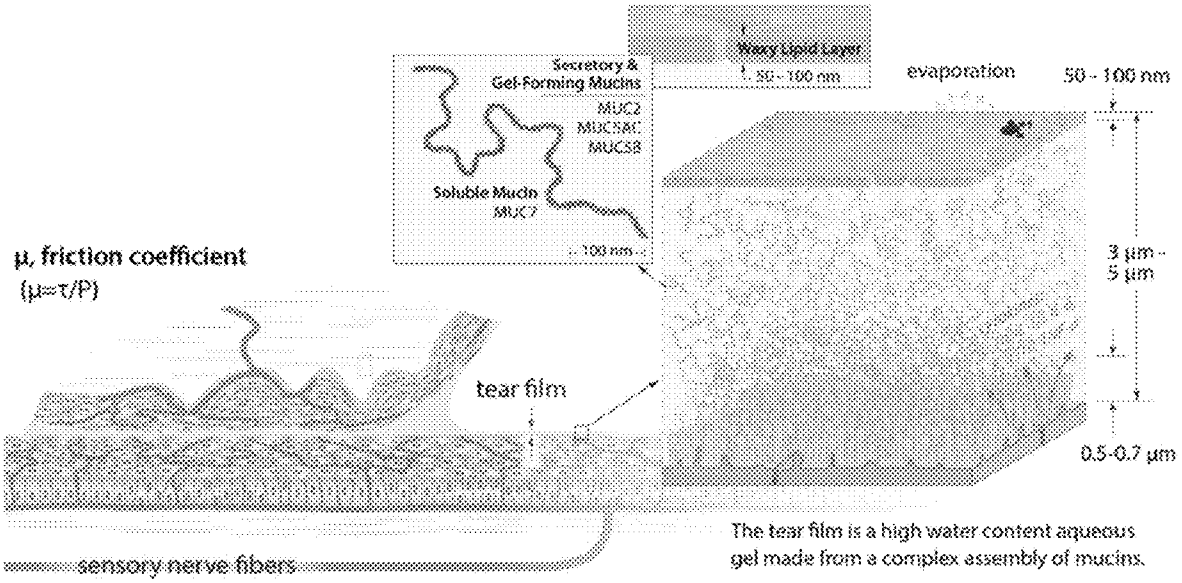
FIG. 1, Table 1, illustrates a list of the mucins found in the ocular environment.
FIG. 2 is a schematic of the corneal epithelium, tear film, mucins associated with the ocular surface, including mucin MUC20 secreted between cells, and the waxy lipid layer.

For convenience, before further description of the present disclosure, certain terms used in the specification, examples and appended claims are collected here. It is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims. These definitions should be read in light of the remainder of the disclosure and understood as by a person of skill in the art. Unless defined otherwise, all technical and scientific terms used herein have the same meaning as commonly understood by a person of ordinary skill in the art. The terms used throughout this specification are defined as follows, unless otherwise limited in specific instances.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biochemistry, molecular biology, genetics, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only and is not intended to be limiting. It is also possible in the present disclosure that steps can be executed in different sequence where this is logically possible.

The articles "a," "an" and "the" are used to refer to one or to more than one (i.e., to at least one) of the grammatical object of the article.

As used herein, "about," "approximately," and the like, when used in connection with a numerical variable, generally refers to the value of the variable and to all values of the variable that are within the experimental error (e.g., within the 95% confidence interval for the mean) or within +/−10% of the indicated value, whichever is greater.

The terms "comprise", "comprising", "including" "containing", "characterized by", and grammatical equivalents thereof are used in the inclusive, open sense, meaning that additional elements may be included. It is not intended to be construed as "consists of only."

As used herein, "subject" refers to any living entity comprised of at least one cell. A living organism can be as simple as, for example, a single isolated eukaryotic cell or cultured cell or cell line, or as complex as a mammal, including a human being, and animals (e.g., vertebrates, amphibians, fish, mammals, e.g., cats, dogs, horses, pigs, cows, sheep, rodents, rabbits, squirrels, bears, primates (e.g., chimpanzees, gorillas, and humans).

As used herein, the terms "treating" and "treatment" can refer generally to obtaining a desired pharmacological and/or physiological effect. The effect can be, but does not necessarily have to be, prophylactic in terms of preventing or partially preventing a disease, symptom or condition thereof. The effect can be therapeutic in terms of a partial or complete cure of a disease, condition, symptom or adverse effect attributed to the disease, disorder, or condition. The term "treatment" as used herein can include any one or more of the following: (a) preventing the disease from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain.

As used herein, "preventative" and "prevent" refers to hindering or stopping a disease or condition before it occurs, even if undiagnosed, or while the disease or condition is still in the sub-clinical phase.

"Polymers" are understood to include, but are not limited to, homopolymers, copolymers, such as for example, block, graft, random and alternating copolymers, terpolymers, etc. and blends and modifications thereof.

As used herein, the term "disease" refers to an interruption, cessation, or disorder of body function, systems, or organs.

As used herein, “derivative” refers to a chemical compound or molecule made from a parent compound by one or more chemical reactions.

Discussion

The present disclosure provides for compositions including at least one type of water-soluble polymer having a molecular weight of about 10 kDa to 10,000 kDa, methods of making the water-soluble polymer, structures having the water-soluble polymer disposed thereof, and methods of use thereof.

The present disclosure provides for water-soluble polymers having high molecular weights (e.g., a molecular weight of about 10 kDa to 10,000 kDa), and application of the water-soluble polymer for gelation and restoration of the functional biological properties of mucinated networks and surfaces. Embodiments of the water-soluble polymer can have one or more of the following characteristics: (1) Mucoadhesion: capable of forming covalent or non-covalent interactions (e.g., non-covalent interactions can be described as supramolecular interactions including, but not limited to, hydrogen bonding, ionic bonds, van Der Waals interactions, hydrophobic interactions, and macromolecular chain entanglement) with naturally occurring mucins; (2) Mucolability: the interactions between the water-soluble polymers and the mucins should typically be reversible, such that these interactions are reversed by mechanical force, background hydrolysis, redox reactions, or exchange with other interactions; and (3) Mucointegration: because of their ability to form interactions with natural mucins and because of their similar degrees of hydrophilicity to natural mucins, the water-soluble polymer are capable of integrating into mucin networks and/or interacting with membrane-bound mucins. The combination of these three characteristics allows the materials described herein to augment the hydration and rheology of mucinated surfaces in vivo. The water-soluble polymers of the present disclosure are designed to interact weakly with mucins, either via rapidly reversible interactions or by forming only a minimal number of interactions with mucins.

The water-soluble polymer of the present disclosure can be synthesized from the polymerization of hydrophilic monomers, yielding highly water-soluble polymers. In an aspect, the water-soluble polymer can have overall molecular weight of about 10 kDa to 10,000 kDa or about 100 kDa to 10,000 kDa. The majority (e.g., greater than 50 weight percent or about 75 to 99.9 weight percent of the molecular weight of the water soluble polymer) of the molecular weight of these polymers is derived from inert, hydrophilic functionality in the backbone (e.g., N,N-dimethylacrylamide). The functionalities of the monomers and/or functional groups on monomers can be selected based on the ability to restore shear-thinning behavior of mucinous gels by forming weak, transient, reversible interactions with mucins and with one another. These transient interactions can be covalent (e.g., boronate ester formation, disulfide formation) or non-covalent (e.g., hydrogen bonding, calcium bridging via carboxylates), or a combination thereof. In other words, a portion of the units of the polymer are mucin-binding units. In an example, these interactions can be accomplished through polymers comprised of N,N-dimethylacrylamide, acrylic acid, 3-(acrylamido)phenylboronic acid, and pyridyl disulfide acrylamide, respectively. In addition, the water-soluble polymer of the present disclosure could also be composed of mixtures of hydrophobic and hydrophilic monomers (e.g., via polymerization of acrylates or styrenics and maleimides), provided the overall polymer is water-soluble. In an aspect, the functionalities (e.g., mucin-binding units such as monomers and/or functional groups) responsible for the transient interactions with mucins or between the water-soluble polymers of the present disclosure are typically sparsely distributed throughout the backbone to constitute about 0.1% to 50%, about 0.1% to 40%, about 0.1% to 35%, about 0.1% to 30%, about 0.1% to 25% of the overall molecular weight of the water-soluble polymer. In an aspect, the low content of monomers/functional groups can be isolated in specific regions of the polymers, where the binding functionalities exist in gradient-type fashion along the polymer backbone or are isolated to regions primarily or solely at one or both ends of the polymers (e.g., terminally located) or only in the middle region of the polymer (e.g., centrally located). In this way, the weight percent of the mucin-binding units can be from very low (e.g., 0.1 to 1 weight percent) to anywhere within the 0.1 to 25 weight percent (e.g., about 0.1 to 25, about 0.1 to 20, about 0.1 to 15, about 0.1 to 10, about 0.1 to 5, about 0.1 to 2, about 0.1 to 1, about 0.1 to 0.5, about 1 to 25, about 1 to 20, about 1 to 15, about 1 to 10, about 1 to 5, about 1 to 2,) of the overall molecular weight of the water-soluble polymer.

The term “water soluble” as in a “water-soluble polymer” is any polymer that is soluble in water at room temperature. Typically, a solution of a water-soluble polymer will transmit at least about 75%, more preferably at least about 95%, of light transmitted by the same solution after filtering. On a weight basis, a water-soluble polymer will preferably be at least about 35% (by weight) soluble in water, more preferably at least about 50% (by weight) soluble in water, still more preferably about 70% (by weight) soluble in water, and still more preferably about 85% (by weight) soluble in water. It is most preferred the water-soluble polymer is about 95% (by weight) soluble in water or completely soluble in water.

In one aspect, the present disclosure provides an ophthalmic solution including a water-soluble polymer. In one aspect, the present disclosure provides a method of treating or preventing a condition in an eye of a subject comprising administering a therapeutically effective amount of the ophthalmic solution disclosed herein to the eye, whereby the water-soluble polymer forms non-covalent interactions or reversible-covalent bonds with mucins or mucin-binding proteins. In another aspect, the water-soluble polymer can form a layer on a structure or device, where the device is used in mucin environments.

In an aspect, the composition includes a water-soluble polymer having a molecular weight of about 10 kDa to 10,000 kDa or about 100 kDa to 10,000 kDa. In an aspect, the composition can include other types of water-soluble polymers. It should be noted that in much of the discussion herein, reference is made to “first water-soluble polymer” but in compositions including two or more types of water-soluble polymers, the description provided herein for “first water-soluble polymer” equally applies to the other types of water-soluble polymers, where the two types of water-soluble polymers are chemically different.

The first water-soluble polymer includes a plurality of backbone units and at least one first type of a mucin binding unit. The backbone units comprise greater than 50% or about 75 to 99.9% of the first water-soluble polymer based on molecular weight. The first type of mucin-binding unit comprises 1 unit up to 50% or about 0.1 to 25% of the first water-soluble polymer based on molecular weight. In other aspects, the first water-soluble polymer can include a second type or a third type of mucin-binding unit. Each type of mucin-binding unit can be 1 unit up to 25%, 1 functional unit to about 5%, about 0.1 to 25%, about 0.1 to 20%, about 0.1 to 15%, about 0.1 to 10%, about 0.1 to 5% or about 0.1 to 1% of the first water-soluble polymer based on molecular weight.

In an embodiment, the first water-soluble polymer can be linear or non-linear such as star-like, branched, hyperbranched, comb/brush-like, graph copolymer, bottle brush-like, or cyclic. In one embodiment, the first water-soluble polymer can be a polyelectrolyte, polyampholyte, or polyzwitterion.

In an aspect, the backbone unit can include monomer units, copolymers including the monomer units, or both monomer units and copolymer unities including monomer units. In an aspect, the first water-soluble polymer can be a block copolymer, a random copolymer, a statistical copolymer, an alternating copolymer, or a gradient copolymer. In an aspect, the first water-soluble polymer is a block copolymer such as a AB diblock copolymer or a ABA triblock copolymer. Optionally the mucin binding unit is isolated on the A block of the AB diblock copolymer or A block of the ABA triblock copolymer. In an aspect, the A and B blocks of the AB or ABA block copolymers contain a mixture of comonomer units. In an aspect, the comonomer units within the A or B blocks can be arranged in alternating, random, statistical, or gradient fashion. In another aspect, one or more blocks of the copolymer can be water-insoluble as long as the overall copolymer is water-soluble. For example, one of A block or B block in a AB diblock copolymer or ABA triblock copolymer can be water-insoluble, where the copolymer itself is water-soluble.

A gradient copolymer is a polymer with more than one type of monomer unit where the frequency of occurrence of at least one monomer unit changes gradually along the polymer chain. A statistical copolymer is a copolymer in which the sequential distribution of the monomeric units obeys known statistical laws and is based on relative reactivities.

In an aspect, the monomer unit can be selected from: an acrylamide monomer, a methacrylamide monomer, an acrylate monomer, a methacrylate monomer, a styrenic monomer, a vinyl pyridine monomer, a maleimide monomer, a maleic anhydride-derived monomer, a vinyl ester monomer, a vinyl amide monomer, a vinyl halide monomer, or a derivative of anyone of these. In a particular aspect, the backbone unit can include a monomer unit or a copolymer including the monomer unit, where the monomer unit is selected from: acrylamide, N,N-dimethylacrylamide, N,N-dialkylacrylamides, N-alkylacrylamides, N,N-dialkyl methacrylamides, N-alkyl methacrylamides, alkyl methacrylates, alkyl acrylates, oligo(ethylene glycol) acrylate, oligo(ethylene glycol) methacrylate, oligo(ethylene glycol) acrylamide, or oligo(ethylene glycol) methacrylamide, other substituted acrylates (e.g., the substitution (R) includes the functionality such as hydroxy group, amine group, carboxylate group, sulfonate group, and the like), other substituted methacrylates (e.g., the substitution (R) includes the functionality such as hydroxy group, amine group, carboxylate group, sulfonate group, and the like). In a specific aspect, the backbone unit is N,N-dimethylacrylamide.

Each type (e.g., first type, second type, third type) of mucin-binding unit can be functionalized so the water-soluble polymer has the characteristic of altering the hydration, rheology, or both of a mucin-based polymer, a second water-soluble polymer, or a combination thereof. The characteristic of altering the hydration, rheology, or both can be achieved through mucoadhesion, mucolability, mucointegration, or a combination thereof, as described herein.

In an aspect, the mucin-binding unit can include a monomer unit, copolymers that include the monomer unit, or both, where the monomer unit includes a functional group bonded to the monomer, where the functional group can be a boronic acid group, a carboxylate group, a carboxylic acid group, a hydrogen-bonding group, a hydrophobic group, or a group capable of forming disulfide linkages. In one embodiment, the plurality of functional groups is distributed in the first water-soluble polymer in homogenous, random, gradient, or blocky order and in a particular aspect, at a terminal end of the water-soluble polymer.

Each type of mucin-binding unit can be a monomer unit or segments of copolymers that include the monomer unit. The monomer unit can be selected from: acrylic acid, methacrylic acid, 4-vinylbenzoic acid, 4-(acrylamido)phenylboronic acid, 3-(acrylamido)phenylboronic acid, (2-(3-acrylamidopropanamido)phenyl)boronic acid (APAPBA), 2-(acrylamido)phenylboronic acid, 4-vinylphenylboronic acid, 3-vinylphenylboronic acid, 2-vinylphenylboronic acid, 2-(pyridin-2-yldisulfaneyl)ethyl methacrylate, pyridyl disulfide ethyl acrylate, pyridyl disulfide ethyl acrylamido, pyridyl disulfide alkyl (e.g. ethyl) methacrylamido, 2-(pyridin-2-yldisulfaneyl)ethyl acrylate, 2-(pyridin-2-yldisulfaneyl)ethyl acrylamido, 2-(pyridin-2-yldisulfaneyl)ethyl methacrylate, or 2-(pyridin-2-yldisulfaneyl)ethyl methacrylate, N-(2-(tritylthio)ethyl)acrylamide, halogenated versions of each of these, or a derivative of any one of these or copolymer of anyone of these.

In an aspect, the first water-soluble polymer can have a chemical structure such as:

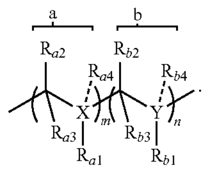

In an aspect, unit a is the backbone unit and m is greater than 50% or about 75 to 99.9% of the first water-soluble polymer based on molecular weight. In an aspect, m and n, independently on one another can be about 1000 to 100,000. Unit b is a first type of mucin-binding unit and n is 1 unit up to 50% or about 0.1 to 25% (or another range as provided herein such as about 0.1 to 10%, about 0.1 to 15%, about 1 to 10%, about 1 to 15%, about 5 to 10%, about 5 to 15%, about 5 to 20%, about 5 to 25% and so on) of the first water-soluble polymer based on molecular weight. Unit a and unit b are different from one another. The dashed lines for $R_{a4}$ and $R_{b4}$ indicated that this is optionally present based on X and Y, respectively.

In an aspect, $R_{a1}$, $R_{a2}$, $R_{a3}$, $R_{a4}$, $R_{b1}$, $R_{b2}$, $R_{b3}$, and $R_{b4}$, independently of one another, can be H, —$OR_1$, —$NR_1R_2$, —$N^+(R_1)_3$, —$N^+(R_1)_2(R_2)$, —$N^+(R_1)(R_2)(R_3)$, —$S(O)_2R_1$, —$S(O)_2OR_1$, —$S(O)_2NR_1R_2$, —$NR_1S(O)_2R_2$, —$NR_1C(O)R_2$, —$C(O)R_1$, —$C(O)OR_1$, —$C(O)NR_1R_2$, —$NR_1C(O)OR_2$, —$NR_1C(O)NR_1R_2$, —$OC(O)NR_1R_2$, —$NR_1S(O)_2NR_1R_2$, —$C(O)NR_1S(O)_2NR_1R_2$, catechol, a boronic acid group, and a pyridyl disulfide group, where each $R_1$, $R_2$, and $R_3$ is independently H or linear or branched $C_{1-18}$ alkyl as well as —$C(O)OCH_2CH_2$—OH, —$C(O)OCH_2CH_2$—$N(CH_3)_2$, —$C(O)OCH_2CH_2$—$N^+(CH_3)_3$, —$C(O)OCH_2CH_2$—$OSO_3$—, —$C(O)OCH_2CH_2$—$OSO_3H$, —C(O)OCH$_2$CH$_2$—SO$_3$—, —C(O)OCH$_2$CH$_2$—SO$_3$H, —C(O)N(H)C((CH$_3$)$_2$)CH$_2$SO$_3$—, or —C(O)N(H)C((CH$_3$)$_2$)CH$_2$SO$_3$H.

In an aspect, X can be N or C and Y can be C or N. In a particular aspect, X and Y are C.

In another aspect, the first water-soluble polymer has chemical structure such as:

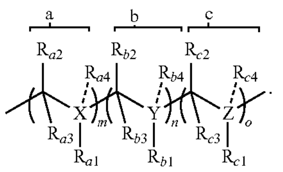

In an aspect, unit a can be the backbone unit and m is greater than 50% or about 75 to 99.9% of the first polymer based on molecular weight. In an aspect, m, n and o, independently on one another can be about 1000 to 100,000. Unit b can be a first type of mucin-binding unit and n is 1 unit up to 50% or about 0.1 to 24% (or another range as provided herein) of the first polymer based on molecular weight. Unit c is the second type of mucin binding unit and o is 1 unit up to 50% or about 0.1 to 24% (or another range as provided herein) of the first polymer based on molecular weight. Unit a and unit b are different from one another or unit a, unit b, and unit c are different than one another. The dashed lines for $R_{a4}$, $R_{b4}$, and $R_{c4}$ indicated that this is optionally present based X, Y, and Z, respectively. In an aspect, unit c can be responsible for mucin binding or can be responsible for further enhancing the hydrophilicity of the backbone (e.g., by introducing charge), for example.

In an aspect, $R_{a1}$, $R_{a2}$, $R_{a3}$, $R_{a4}$, $R_{b1}$, $R_{b2}$, $R_{b3}$, $R_{b4}$, $R_{c1}$, $R_{c2}$, $R_{c3}$, and $R_{c4}$, independently of one another, can be H, —OR$_1$, —NR$_1$R$_2$, —N$^+$(R$_1$)$_3$, —N$^+$(R$_1$)$_2$(R$_2$), —N$^+$(R$_1$)(R$_2$)(R$_3$), —S(O)$_2$R$_1$, —S(O)$_2$OR$_1$, —S(O)$_2$NR$_1$R$_2$, —NR$_1$S(O)$_2$R$_2$, —NR$_1$C(O)R$_2$, —C(O)R$_1$, —C(O)OR$_1$, —C(O)NR$_1$R$_2$, —NR$_1$C(O)OR$_2$, —NR$_1$C(O)NR$_1$R$_2$, —OC(O)NR$_1$R$_2$, —NR$_1$S(O)$_2$NR$_1$R$_2$, —C(O)NR$_1$S(O)$_2$NR$_1$R$_2$, catechol, a boronic acid group, and a pyridyl disulfide group, where each R$_1$, R$_2$, and R$_3$ is independently H or linear or branched C$_{1-13}$ alkyl as well as —C(O)OCH$_2$CH$_2$—OH, —C(O)OCH$_2$CH$_2$—N(CH$_3$)$_2$, —C(O)OCH$_2$CH$_2$—N+(CH$_3$)$_3$, —C(O)OCH$_2$CH$_2$—OSO$_3$—, —C(O)OCH$_2$CH$_2$—OSO$_3$H, —C(O)OCH$_2$CH$_2$—SO$_3$—, —C(O)OCH$_2$CH$_2$—SO$_3$H, —C(O)N(H)C((CH$_3$)$_2$)CH$_2$SO$_3$—, or —C(O)N(H)C((CH$_3$)$_2$)CH$_2$SO$_3$H, In an aspect, X can be N or C, where Y can be C or N and where Z can be N or C. In a particular aspect, X, Y, and Z are C.

In another aspect, the first water-soluble polymer has chemical structure such as:

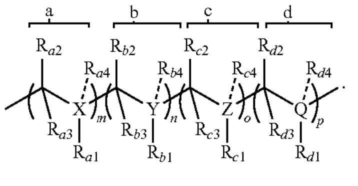

In an aspect, unit a can be the backbone unit and m is greater than 50% or about 75 to 99.9% of the first water-soluble polymer based on molecular weight. In an aspect, m, n and o, independently on one another can be about 1000 to 100,000. Unit b can be the first type of mucin-binding unit and n is 1 unit up to 50% or about 0.1 to 24% of the first polymer based on molecular weight. Unit c can be the second type of mucin-binding unit and o is about 0.1 to 24% of the first water-soluble polymer based on molecular weight. Unit d can be the third type of mucin-binding unit and o is 1 unit up to 50% or about 0.1 to 24% of the first water-soluble polymer based on molecular weight. Unit a and unit b can be different from one another, unit a, unit b, and unit c can be different than one another, or unit a, unit b, unit c, and unit d can be different than one another. The dashed lines for $R_{a4}$, $R_{b4}$, $R_{c4}$, and $R_{d4}$ indicated that this is optionally present based X, Y, Z, and Q respectively. In an aspect, unit c and/or unit d can be responsible for mucin binding or can be responsible for further enhancing the hydrophilicity of the backbone (e.g., by introducing charge), for example.

In an aspect, $R_{a1}$, $R_{a2}$, $R_{a3}$, $R_{a4}$, $R_{b1}$, $R_{b2}$, $R_{b3}$, $R_{b4}$, $R_{c1}$, $R_{c2}$, $R_{c3}$, $R_{c4}$, $R_{d1}$, $R_{d2}$, $R_{d3}$, and $R_{d4}$, independently of one another, can be H, —OR$_1$, —NR$_1$R$_2$, —N$^+$(R$_1$)$_3$, —N$^+$(R$_1$)$_2$(R$_2$), —N$^+$(R$_1$)(R$_2$)(R$_3$), —S(O)$_2$R$_1$, —S(O)$_2$OR$_1$, —S(O)$_2$NR$_1$R$_2$, —NR$_1$S(O)$_2$R$_2$, —NR$_1$C(O)R$_2$, —C(O)R$_1$, —C(O)OR$_1$, —C(O)NR$_1$R$_2$, —NR$_1$C(O)OR$_2$, —NR$_1$C(O)NR$_1$R$_2$, —OC(O)NR$_1$R$_2$, —NR$_1$S(O)$_2$NR$_1$R$_2$, —C(O)NR$_1$S(O)$_2$NR$_1$R$_2$, catechol, a boronic acid group, and a pyridyl disulfide group, where each R$_1$, R$_2$, and R$_3$ is independently H or linear or branched C$_{1-13}$ alkyl as well as —C(O)OCH$_2$CH$_2$—OH, —C(O)OCH$_2$CH$_2$—N(CH$_3$)$_2$, —C(O)OCH$_2$CH$_2$—N$^+$(CH$_3$)$_3$, —C(O)OCH$_2$CH$_2$—OSO$_3$—, —C(O)OCH$_2$CH$_2$—OSO$_3$H, —C(O)OCH$_2$CH$_2$—SO$_3$—, —C(O)OCH$_2$CH$_2$—SO$_3$H, —C(O)N(H)C((CH$_3$)$_2$)CH$_2$SO$_3$—, or —C(O)N(H)C((CH$_3$)$_2$)CH$_2$SO$_3$H, In an aspect, X can be N or C, where Y can be C or N, where Z can be N or C, and where Q can be N or C. In a particular aspect, X, Y, Z and Q are C.

In one aspect, the water-soluble polymer of the present disclosure can be prepared via aqueous reversible-deactivation radical polymerization (See, Chem, 2017, 2(1), 93-101). In one embodiment, the polymeric material is prepared via macromolecular design by interchange of xanthate (MADIX) polymerization. In one embodiment, the polymeric material is prepared via photoiniferter polymerization. These materials with controlled molecular weight could also be derived through other controlled radical polymerization methods, such as atom transfer radical polymerization, and nitroxide mediated polymerization. Additionally, these materials could be derived through conventional radical, anionic, cationic, ring-opening, and ring-opening metathesis polymerization.

In particular, the present disclosure provides for synthetic methods of making the first water-soluble polymer as provided herein by polymerizing a backbone unit and at least one mucin-binding unit to form the first water-soluble polymer. The polymerization can be a radical polymerization, conventional radical polymerization, reversible-deactivation radical polymerization, reversible addition-fragmentation chain transfer (RAFT) polymerization, macromolecular design by interchange of xanthate (MADIX) polymerization, photoiniferter polymerization, atom transfer radical polymerization (ATRP), or stable free radical polymerization (SFRP) as well as by post-polymerization modification (e.g., by modification of monomer units that contain activated ester groups).

A typical photoiniferter polymerization initiated by a trithiocarbonate is as follows. targeting $M_n \geq 5.00 \times 10^6$ g/mol). DMA (394 mg, 3.97 mmol) and trithiocarbonate iniferter (20.0 μg, $7.45\times10^{-5}$ mmol from 1.00 mg/mL dimethyl sulfoxide (DMSO) stock solution) were dissolved in water (1.70 mL, 2 M [DMA]) in a 10 mL Schlenk flask, and N,N-Dimethylformamide (DMF) (0.100 mL) was added as an internal standard. The iniferter stock solution was stored between 2 and 6° C. for further use. Argon was bubbled through the polymerization solution for 20 min. The reaction vessel was positioned 2.50 cm from the ultraviolet (UV) light source for an intensity of 7.0 mW/cm$^2$, and polymerization was initiated upon irradiation. Monomer conversion was determined by $^1$H NMR spectroscopy, monitoring the disappearance of the DMA vinyl peaks (d, 1H, 5.60 ppm) relative to DMF (s, 1H, 8.02 ppm). Each reaction aliquot was dried by lyophilization and dissolved in SEC solvent (1 mg/mL) at least 24 h prior to molecular weight characterization.

An example chain extension polymerization that demonstrates the ability to make high molecular weight block copolymers via photoiniferter polymerization is as follows. DMA (417 mg, 4.20 mmol) and trithiocarbonate iniferter (0.100 mg, $3.72\times10^{-4}$ mmol from 1.00 mg/mL DMSO stock solution) were dissolved in water (3.70 mL 1 M [DMA]) in a 10 mL Schlenk flask and DMF (0.100 mL) was added as an internal standard. Argon was bubbled through the polymerization solution for 20 min. The reaction vessel was positioned 2.50 cm from the UV light source for an intensity of 7.0 mW/cm$^2$ and polymerization was initiated upon irradiation. The reaction was irradiated for 24 h and a small amount was removed to determine monomer conversion via $^1$H NMR spectroscopy by monitoring the disappearance of the vinyl, DMA peaks (d, 1H, 5.60 ppm) relative to DMF (s, 1H, 8.02 ppm) and to characterize molecular weight via SEC. The polymerization of the poly(DMA) (PDMA) first block reached >95% monomer conversion. DMA (420 mg, 4.24 mmol) was dissolved in water (3.10 mL), DMF (0.100 mL), and the preceding PDMA polymerization mixture. Argon was bubbled through the viscous solution for 20 min, and chain extension was initiated upon irradiation.

In an aspect, the present disclosure includes a method where the mucin-binding unit or combination of mucin binding units is incorporated into the copolymer by a post-polymerization reaction of copolymer units. The reactive monomer units, which can be reacted with a small molecule to add the mucin-binding unit, may include activated esters, (e.g., N-hydroxylsuccinimide esters, pentafluorophenyl esters, hydroxybenzotriazole esters, nitrophenol esters, phthalimide esters), azido groups, alkyne groups, halogen groups, carboxylic acid groups, etc.).

Examples

Cell Model Studies of Ultra-High Molecular Weight Polymers and Mucin:

A Gemini model of corneal epithelial cells (self-mated and matched) with intact membrane-bound mucins and glycocalyces (including MUC1, MUC4, and MUC16) and purified gel-forming secretory mucin, MUC2, was evaluated in the presence and absence of ultra-high molecular weight polymers containing mucoadhesive moieties. These experiments were performed under physiological contact pressures for 300 to 1000+ cycles of reciprocated sliding at 1 mm/s on a micro-biotribometer. During the experiment, the cell culture media was continuously replaced with fresh media without mucin or polymer to simulate tear film turnover in the ocular environment. With the addition of ultra-high molecular weight mucoadhesive polymers, friction reductions were observed, and friction coefficients remained lower for significantly more cycles than in experiments with mucin alone, indicating long-lasting mucoadhesion after application of ultra-high molecular weight mucomimetic polymers.

Experimental Setup

A Gemini model of corneal epithelial cells was achieved via surface functionalization of fibronectin-coated glass-bottom culture dishes and collagen-conjugated polyacrylamide membrane probes. Confocal imaging and biotribology: Confluent monolayers of corneal epithelial cells were carefully imaged, characterized, and confirmed on both surfaces (glass-bottom culture dish and membrane probe) prior to experiments. The culture condition was maintained at 37±0.2° C., 5% $CO_2$, and ~100% humidity using a custombuilt stage incubator. A normal load of 300 μN was applied between the two epithelial cell surfaces resulting in-600 Pa mean contact pressure across the interface. The contact pressure was determined by dividing the normal load by the measured contact area of the corneal cells coated membrane probes. The corneal cell monolayer on the culture dish, mounted on a reciprocating stage, slid against the cell monolayer counterpart on the membrane probe for 300 cycles (30 min) at a speed of 1 mm/s, with a 3 mm stroke length. The normal and friction force was recorded from the defection of the cantilever at a data acquisition rate of 100 Hz. During the tribology experiment, syringe pumps were used to simultaneously infuse and withdraw cell culture without mucin or polymer present at a rate of 18.5 μL/min to investigate integration and adhesion with cell-bound mucin.

Micro-Rheology of Ultra-High Molecular Weight Polymers and Mucin:

Micro-rheology experiments using magnetic tweezers showed a yield stress for a mixture of ultra-high molecular weight (UHMW) mucoadhesive polymer and purified gel-forming secretory mucin MUC2 that is below the critical thresholds known to produce proinflammatory cytokines (<40 Pa) and apoptosis (<100 Pa). Importantly, rheological measurements conducted on either MUC2 or UHMW mucoadhesive polymer alone showed viscous fluid characteristics (G">G') over a large frequency range, but mixtures of these two showed successful dynamic gel formation and a crossover of the storage/loss moduli (G'>G"). Experimental Setup A nickel base soft magnetic alloy rod (ASTM A753 Type 4, MIL N-14411C Comp 1) was machined to have a chisel tip of width-100 μm. The tip geometry was designed to achieve optimal horizontal magnetic fields at the vicinity of the tip. The rod was then wound with 1200 turns of AWG 22 copper magnet wire over a length of 120 mm. The whole apparatus was mounted on a manual stage manipulator (OptoSigma) alongside an inverted Nikon AiR confocal microscope. Experiments were conducted under temperature-controlled and high humidity conditions to prevent drying or water loss of the sample. A current of 1 A was applied for all measurements. At these settings, electrical resistance heating of the rod is negligible. Fluorescently tagged and superparamagnetic particles, 5.8 μm diameter (COMPEL™ UMDG002/UMC3F, COOH functionalized beads, Bangs Laboratories Inc., Fishers, Indiana, USA) were added at a concentration of ~0.02 volume fraction and vortex mixed for 15 s to ensure uniform dispersion. This working concentration has been tested to ensure measurable single-particle trajectories. Data of magnetic probe dynamics were captured using a high-speed electron multiply CCD camera (Andor iXon Life 888, Oxford Instruments, U.K.) at a rate of 100 frames s−1. Horizontal displacements (in the x-direction) are predominant. The force applied on probe particles was calibrated by tracking particle motion in an 80 wt. % solution of glycerol (Sigma-Aldrich) in water, which has dynamic viscosity $\eta$=0.060 to Pa-s, which was confirmed using bulk rheology measurements. Stokes drag is used to model the force on a particle as a function of velocity, which is measured as a function of position through particle tracking.

In particular, the present disclosure provides for, but is not limited to, the following aspects.

Aspect 1. The present disclosure provides for a composition comprising: a first water-soluble polymer having a molecular weight of about 10 kDa to 10,000 kDa, wherein the first water-soluble polymer includes a plurality of backbone units and at least one first type of a mucin-binding unit, wherein the backbone units comprise greater than 50% of the first water-soluble polymer based on molecular weight, wherein the first type of mucin-binding unit comprises of 1 unit up to 50% of the first water-soluble polymer based on molecular weight, wherein the first type of mucin-binding unit is functionalized so the water-soluble polymer has the characteristic of altering the hydration, rheology, or both of a mucin polymer, a second water-soluble polymer, or a combination thereof, wherein altering the hydration, rheology, or both is achieved through mucoadhesion, mucolability, mucointegration, or a combination thereof.

Aspect 2. The composition of claim aspect 1, wherein the backbone unit comprises monomer units, copolymers including the monomer units, or both the monomer units and the copolymers, wherein the monomer unit is selected from the group consisting of: an acrylamide monomer, a methacrylamide monomer, an acrylate monomer, a methacrylate monomer, a styrenic monomer, a vinyl pyridine monomer, a maleimide monomer, a maleic anhydride-derived monomer, a vinyl ester monomer, a vinyl ether monomer, a vinyl amide monomer, a vinyl amine monomer, a vinyl halide monomer, or a derivative of anyone of these.

Aspect 3. The composition of aspect 1, wherein the backbone unit comprises a monomer unit, a copolymer including the monomer unit or both, wherein the monomer unit is selected from the group consisting of: acrylamide, N,N-dimethylacrylamide, N,N-dialkylacrylamides, N-alkylacrylamides, N,N-dialkyl methacrylamides, N-alkyl methacrylamides, poly(ethlylene glycol) acrylate, poly(ethylene glycol) methacrylate, poly(ethylene glycol) acrylamide, and poly(ethylene glycol) methacrylamide.

Aspect 4. The composition of aspect 1, wherein the backbone unit is N,N-dimethylacrylamide.

Aspect 5. The composition of aspect 1, wherein the mucin-binding unit comprises monomer units, copolymers that include the monomer units, or both, wherein the monomer unit is selected from the group consisting of: acrylic acid, methacrylic acid, 4-vinylbenzoic acid, 4-(acrylamido)phenylboronic acid, 3-(acrylamido)phenylboronic acid, (2-(3-acrylamidopropanamido)phenyl)boronic acid (APAPBA), 2-(acrylamido)phenylboronic acid, 4-vinylphenylboronic acid, 3-vinylphenylboronic acid, 2-vinylphenylboronic acid, 2-(pyridin-2-yldisulfaneyl)ethyl methacrylate, pyridyl disulfide ethyl acrylate, pyridyl disulfide ethyl acrylamido, pyridyl disulfide alkyl (e.g. ethyl) methacrylamido, 2-(pyridin-2-yldisulfaneyl)ethyl acrylate, 2-(pyridin-2-yldisulfaneyl)ethyl acrylamido, 2-(pyridin-2-yldisulfaneyl)ethyl methacrylate, or 2-(pyridin-2-yldisulfaneyl)ethyl methacrylate, N-(2-(tritylthio)ethyl)acrylamide, a monomer including one or more boronic acid groups, a monomer containing one or more disulfide-forming groups, a halogenated versions of each of these, or a derivative of any one of these or copolymer of anyone of these.

Aspect 6. The composition of aspect 1, wherein the mucin-binding unit comprises monomer units, copolymers that include the monomer units, or both, wherein the monomer unit includes a functional group selected from the group consisting of: a boronic acid group, a carboxylate group, a carboxylic acid group, a hydrogen-bonding group, a hydrophobic group, a 1,2-diol group, a 1,3-diol group, a group capable of forming disulfide linkages or a derivative of any one of these.

Aspect 7. The composition of aspect 1, wherein the first water-soluble polymer includes a second type of mucin-binding unit, wherein the second type of mucin-binding unit comprises monomer units, copolymers that include the monomer units, or both, wherein the monomer unit is selected from the group consisting of: acrylic acid, methacrylic acid, 4-vinylbenzoic acid, 4-(acrylamido)phenylboronic acid, 3-(acrylamido)phenylboronic acid, (2-(3-acrylamidopropanamido)phenyl)boronic acid (APAPBA), 2-(acrylamido)phenylboronic acid, 4-vinylphenylboronic acid, 3-vinylphenylboronic acid, 2-vinylphenylboronic acid, 2-(pyridin-2-yldisulfaneyl)ethyl methacrylate, pyridyl disulfide ethyl acrylate, pyridyl disulfide ethyl acrylamido, pyridyl disulfide alkyl (e.g. ethyl) methacrylamido, 2-(pyridin-2-yldisulfaneyl)ethyl acrylate, 2-(pyridin-2-yldisulfaneyl)ethyl acrylamido, 2-(pyridin-2-yldisulfaneyl)ethyl methacrylate, or 2-(pyridin-2-yldisulfaneyl)ethyl methacrylate, N-(2-(tritylthio)ethyl)acrylamide, a monomer including one or more boronic acid groups, a monomer containing one or more disulfide-forming groups, a halogenated versions of each of these, or a derivative of any one of these or copolymer of anyone of these, wherein the first type of mucin-binding unit is different than the second type of mucin-binding unit.

Aspect 8. The composition of aspect 7, wherein the first water-soluble polymer includes a third type of mucin-binding unit, wherein the third type of mucin-binding unit comprises monomer units, copolymers that include the monomer units, or both, wherein the monomer unit is selected from the group consisting of: acrylic acid, methacrylic acid, 4-vinylbenzoic acid, 4-(acrylamido)phenylboronic acid, 3-(acrylamido)phenylboronic acid, (2-(3-acrylamidopropanamido)phenyl)boronic acid (APAPBA), 2-(acrylamido)phenylboronic acid, 4-vinylphenylboronic acid, 3-vinylphenylboronic acid, 2-vinylphenylboronic acid, 2-(pyridin-2-yldisulfaneyl)ethyl methacrylate, pyridyl disulfide ethyl acrylate, pyridyl disulfide ethyl acrylamido, pyridyl disulfide alkyl (e.g. ethyl) methacrylamido, 2-(pyridin-2-yldisulfaneyl)ethyl acrylate, 2-(pyridin-2-yldisulfaneyl)ethyl acrylamido, 2-(pyridin-2-yldisulfaneyl)ethyl methacrylate, or 2-(pyridin-2-yldisulfaneyl)ethyl methacrylate, N-(2-(tritylthio)ethyl)acrylamide, a monomer including one or more boronic acid groups, a monomer containing one or more disulfide-forming groups, a halogenated versions of each of these, or a derivative of any one of these or copolymer of anyone of these, wherein the first type of mucin-binding unit is different than the second type of mucin-binding unit, wherein the second type of mucin-binding unit is different than the third type of mucin-binding unit monomer including one or more pyridyl disulfide groups, or a derivative of any one of these.

Aspect 9. The composition of aspect 8, wherein the first type of mucin binding unit comprises 1 functional unit to about 5% of the first water-soluble polymer based on molecular weight; wherein the second type of mucin binding unit comprises 1 functional unit to about 5% of the first water-soluble polymer based on molecular weight; wherein the third type of mucin binding unit comprises 1 functional unit to about 5% of the first water-soluble polymer based on molecular weight.

Aspect 10. The composition of aspect 1, wherein the first water-soluble polymer has a structure that is linear or non-linear, wherein the non-linear structure is selected from the group consisting of star-like, branched, hyperbranched, cyclic, graph copolymer, or bottle brush-like.

Aspect 11. The composition of aspect 1, wherein the first type of mucin binding unit is located solely at one or both terminal ends of the first water-soluble polymer.

Aspect 12. The composition of aspect 1, wherein the first water-soluble polymer is a block copolymer.

Aspect 13. The composition of aspect 1, wherein the first water-soluble polymer is a random copolymer.

Aspect 14. The composition of aspect 1, wherein the first water-soluble polymer is a statistical copolymer.

Aspect 15. The composition of aspect 1, wherein the first water-soluble polymer is an alternative copolymer.

Aspect 16. The composition of aspect 1, wherein the first water-soluble polymer is a gradient copolymer.

Aspect 17. The composition of aspect 12, wherein the block copolymer is an AB diblock copolymer or an ABA triblock copolymer, optionally wherein the mucin-binding units are isolated on the A block of the AB diblock copolymer or A block of the ABA triblock copolymer.

Aspect 18. The composition of aspect 1, wherein the first water-soluble polymer has the following chemical structure:

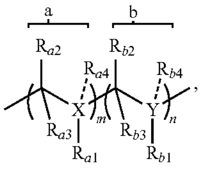

wherein unit a is the backbone unit and m is greater than 50% of the first water-soluble polymer based on molecular weight, wherein unit b is the first type of mucin binding unit and n is 1 unit to about 50% of the first water-soluble polymer based on molecular weight, wherein unit a and unit b are different from one another, $R_{a1}$, $R_{a2}$, $R_{a3}$, $R_{a4}$, $R_{b1}$, $R_{b2}$, $R_{b3}$, and $R_{b4}$, independently of one another, are selected from: H, $-OR_1$, $-NR_1R_2$, $-N^+(R_1)_3$, $-N^+(R_1)_2(R_2)$, $-N^+(R_1)(R_2)(R_3)$, $-S(O)_2R_1$, $-S(O)_2OR_1$, $-S(O)_2NR_1R_2$, $-NR_1S(O)_2R_2$, $-NR_1C(O)R_2$, $-C(O)R_1$, $-C(O)OR_1$, $-C(O)NR_1R_2$, $-NR_1C(O)OR_2$, $-NR_1C(O)NR_1R_2$, $-OC(O)NR_1R_2$, $-NR_1S(O)_2NR_1R_2$, $-C(O)NR_1S(O)_2NR_1R_2$, catechol, a boronic acid group, and a pyridyl disulfide group, where each $R_1$, $R_2$, and $R_3$ is independently H or a linear or branched $C_{1-13}$ alkyl as well as $-C(O)OCH_2CH_2-OH$, $-C(O)OCH_2CH_2-N(CH_3)_2$, $-C(O)OCH_2CH_2-N^+(CH_3)_3$, $-C(O)OCH_2CH_2-OSO_3$, $-C(O)OCH_2CH_2-OSO_3H$, $-C(O)OCH_2CH_2-SO_3-$, $-C(O)OCH_2CH_2-SO_3H$, and $-C(O)N(H)C((CH_3)_2)CH_2SO_3-$, $-C(O)N(H)C((CH_3)_2)CH_2SO_3H$, wherein X is C, and wherein Y is C.

Aspect 19. The composition of aspect 1, wherein the first water-soluble polymer has the following chemical structure:

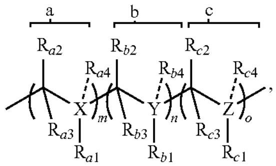

wherein unit a is the backbone unit and m is greater than 50% of the first water-soluble polymer based on molecular weight, wherein unit b is the first type of mucin binding unit and n is 1 unit to about 50% of the first water-soluble polymer based on molecular weight, wherein unit c is the second type of mucin binding unit and o is 1 unit to about 50% of the first water-soluble polymer based on molecular weight, wherein unit a and unit b are different from one another, $R_{a1}$, $R_{a2}$, $R_{a3}$, $R_{a4}$, $R_{b1}$, $R_{b2}$, $R_{b3}$, $R_{b4}$, $R_{c1}$, $R_{c2}$, $R_{c3}$, and $R_{c4}$, independently of one another, can be H, $-OR_1$, $-NR_1R_2$, $-N^+(R_1)_3$, $-N^+(R_1)_2(R_2)$, $-N^+(R_1)(R_2)(R_3)$, $-S(O)_2R_1$, $-S(O)_2OR_1$, $-S(O)_2NR_1R_2$, $-NR_1S(O)_2R_2$, $-NR_1C(O)R_2$, $-C(O)R_1$, $-C(O)OR_1$, $-C(O)NR_1R_2$, $-NR_1C(O)OR_2$, $-NR_1C(O)NR_1R_2$, $-OC(O)NR_1R_2$, $-NR_1S(O)_2NR_1R_2$, $-C(O)NR_1S(O)_2NR_1R_2$, catechol, a boronic acid group, and a pyridyl disulfide group, where each $R_1$, $R_2$, and $R_3$ is independently H or linear or branched $C_{1-18}$ alkyl as well as $-C(O)OCH_2CH_2-OH$, $-C(O)OCH_2CH_2-N(CH_3)_2$, $-C(O)OCH_2CH_2-N^+(CH_3)_3$, $-C(O)OCH_2CH_2-OSO_3-$, $-C(O)OCH_2CH_2-OSO_3H$, $-C(O)OCH_2CH_2-SO_3-$, $-C(O)OCH_2CH_2-SO_3H$, and $-C(O)N(H)C((CH_3)_2)CH_2SO_3-$, $-C(O)N(H)C((CH_3)_2)CH_2SO_3H$, wherein X is C, wherein Y is C, and wherein Z is C.

Aspect 20. The composition of aspect 19, wherein unit a, unit b, and unit c are different from one another.

Aspect 21. The composition of aspect 1, wherein the first water-soluble polymer has chemical structure as shown below:

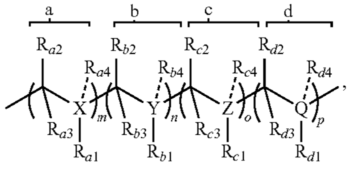

wherein unit a is the backbone unit and m is greater than 50% of the first water-soluble polymer based on molecular weight, wherein unit b is the first type of mucin binding unit and n is 1 unit to about 50% of the first water-soluble polymer based on molecular weight, wherein unit c is the second type of mucin binding unit and o is 1 unit to about 50% of the first water-soluble polymer based on molecular weight, wherein unit d is the second type of mucin binding unit and o is 1 unit to about 50% of the first water-soluble polymer based on molecular weight, wherein unit a and unit b are different from one another, $R_{a1}$, $R_{a2}$, $R_{a3}$, $R_{a4}$, $R_{b1}$, $R_{b2}$, $R_{b3}$, $R_{b4}$, $R_{c1}$, $R_{c2}$, $R_{c3}$, $R_{c4}$, $R_{d1}$, $R_{d2}$, $R_{d3}$, and $R_{d4}$, independently of one another, can be H, $-OR_1$, $-NR_1R_2$, $-N^+(R_1)_3$, $-N^+(R_1)_2(R_2)$, $-N^+(R_1)(R_2)(R_3)$, $-S(O)_2R_1$, $-S(O)_2OR_1$, $-S(O)_2NR_1R_2$, $-NR_1S(O)_2R_2$, $-NR_1C(O)R_2$, $-C(O)R_1$, $-C(O)OR_1$, $-C(O)NR_1R_2$, $-NR_1C(O)OR_2$, $-NR_1C(O)NR_1R_2$, $-OC(O)NR_1R_2$, $-NR_1S(O)_2NR_1R_2$, $-C(O)NR_1S(O)_2NR_1R_2$, catechol, a boronic acid group, and a pyridyl disulfide group, where each $R_1$, $R_2$, and $R_3$ is independently H or linear or branched $C_{1-18}$ alkyl as well as $-C(O)OCH_2CH_2-OH$, $-C(O)OCH_2CH_2-N(CH_3)_2$, $-C(O)OCH_2CH_2-N^+(CH_3)_3$, $-C(O)OCH_2CH_2-OSO_3-$, $-C(O)OCH_2CH_2-OSO_3H$, $-C(O)OCH_2CH_2-SO_3-$, $-C(O)OCH_2CH_2-SO_3H$, and $-C(O)N(H)C((CH_3)_2)CH_2SO_3-$, $-C(O)N(H)C((CH_3)_2)CH_2SO_3H$, wherein X is C, wherein Y is C, wherein Z is C, and wherein Q is C.

Aspect 22. The composition of aspect 21, wherein unit a, unit b, unit c, and unit d are different from one another.

Aspect 23. The composition of aspect 1, wherein the first water-soluble polymer has a molecular weight of about 100 kDa to 10,000 kDa.

Aspect 24. A synthetic method of making the first water-soluble polymer of aspects 1 to 23, comprising: polymerizing a backbone unit and at least one mucin-binding unit to form the first water-soluble polymer of claims 1 to 23.

Aspect 25. The method of aspect 24, wherein the polymerization is cationic polymerization, anionic polymerization, ring-opening polymerization, or coordination polymerization.

Aspect 26. The method of aspect 24, wherein the polymerization is a radical polymerization, conventional radical polymerization, reversible-deactivation radical polymerization, reversible addition-fragmentation chain transfer (RAFT) polymerization, macromolecular design by interchange of xanthate (MADIX) polymerization, photoiniferter polymerization, atom transfer radical polymerization (ATRP), or stable free radical polymerization (SFRP) or optionally the polymerization is a reversible addition-fragmentation chain transfer (RAFT) polymerization, photoiniferter polymerization, or macromolecular design by interchange of xanthate (MADIX) polymerization.

Aspect 27. The method of aspect 24, wherein the backbone unit comprises monomer unit is selected from the group consisting of: an acrylamide monomer, a methacrylamide monomer, an acrylate monomer, a methacrylate monomer, a styrenic monomer, a vinyl pyridine monomer, a maleimide monomer, a maleic anhydride-derived monomer, a vinyl ester monomer, a vinyl ether monomer, a vinyl amide monomer, a vinyl amine monomer, a vinyl halide monomer, or a derivative of anyone of these.

Aspect 28. The method of aspect 24, wherein the backbone unit is selected from the group consisting of: acrylamide, N,N-dimethylacrylamide, N,N-dialkylacrylamides, N-alkylacrylamides, N,N-dialkyl methacrylamides, N-alkyl methacrylamides, poly(ethlylene glycol) acrylate (e.g., oligo(ethylene glycol)acrylate), poly(ethylene glycol) methacrylate (e.g., oligo(ethylene glycol) methacrylate), poly(ethylene glycol) acrylamide (e.g., oligo(ethylene glycol) acrylamide), and poly(ethylene glycol) methacrylamide (e.g., oligo(ethylene glycol) methacrylamide).

Aspect 29. The method of aspect 24, wherein the mucin-binding unit comprises monomer units, copolymers that include the monomer units, or both, wherein the monomer unit includes a functional group selected from the group consisting of: a boronic acid group, a carboxylate group, a carboxylic acid group, a hydrogen-bonding group, a hydrophobic group, a 1,2-diol group, a 1,3-diol group, a group capable of forming disulfide linkages, or a derivative of any one of these.

Aspect 30. The method of aspect 24, wherein the mucin-binding unit is selected from the group consisting of: acrylic acid, methacrylic acid, 4-vinylbenzoic acid, 4-(acrylamido)phenylboronic acid, 3-(acrylamido)phenylboronic acid, (2-(3-acrylamidopropanamido)phenyl)boronic acid (APAPBA), 2-(acrylamido)phenylboronic acid, 4-vinylphenylboronic acid, 3-vinylphenylboronic acid, 2-vinylphenylboronic acid, 2-(pyridin-2-yldisulfaneyl)ethyl methacrylate, pyridyl disulfide ethyl acrylate, pyridyl disulfide ethyl acrylamido, pyridyl disulfide alkyl (e.g. ethyl) methacrylamido, 2-(pyridin-2-yldisulfaneyl)ethyl acrylate, 2-(pyridin-2-yldisulfaneyl)ethyl acrylamido, 2-(pyridin-2-yldisulfaneyl)ethyl methacrylate, or 2-(pyridin-2-yldisulfaneyl)ethyl methacrylate, N-(2-(tritylthio)ethyl)acrylamide, a monomer including one or more boronic acid groups, a monomer containing one or more disulfide-forming groups, a halogenated versions of each of these, or a derivative of any one of these or copolymer of anyone of these.

Aspect 31. The method of aspect 24, wherein the mucin-binding unit includes a functional group selected from the group consisting of: a boronic acid group, a carboxylate group, a carboxylic acid group, a hydrogen-bonding group, a hydrophobic group, a 1,2-diol group, a 1,3-diol group, and a group capable of forming disulfide linkages.

Aspect 32. The method of any one of the aspects, wherein the mucin-binding unit or combination of mucin binding units is incorporated into the copolymer by a post-polymerization reaction of copolymer units.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

Many variations and modifications may be made to the above-described embodiments. All such modifications and variations are intended to be included herein within the scope of this disclosure and protected by the following claims.

The invention claimed is:

1. A composition comprising: an ophthalmic aqueous solution including a first water-soluble polymer, wherein the first water-soluble polymer includes a plurality of backbone units and at least one first type of a mucin-binding unit, wherein the backbone units comprise greater than 50% of the first water-soluble polymer based on molecular weight, wherein the first type of mucin-binding unit comprises of 1 unit up to 50% of the first water-soluble polymer based on molecular weight, wherein the first type of mucin-binding unit comprises monomer units, copolymers that include the monomer units, or both, wherein the monomer unit includes a boronic acid group, wherein the first water-soluble polymer includes a second type of mucin-binding unit, wherein the second type of mucin-binding unit comprises monomer units, copolymers that include the monomer units, or both, wherein the monomer unit is selected from the group consisting of: acrylic acid, methacrylic acid, 4-vinylbenzoic acid, 4-(acrylamido)phenylboronic acid, 3-(acrylamido)phenylboronic acid, (2-(3-acrylamidopropanamido)phenyl) boronic acid (APAPBA), 2-(acrylamido)phenylboronic acid, 4-vinylphenylboronic acid, 3-vinylphenylboronic acid, 2-vinylphenylboronic acid, 2-(pyridin-2-yldisulfaneyl)ethyl methacrylate, pyridyl disulfide ethyl acrylate, pyridyl disulfide ethyl acrylamido, pyridyl disulfide alkyl (e.g. ethyl) methacrylamido, 2-(pyridin-2-yldisulfaneyl)ethyl acrylate, 2-(pyridin-2-yldisulfaneyl)ethyl acrylamido, 2-(pyridin-2-yldisulfaneyl)ethyl methacrylate, or 2-(pyridin-2-yldisulfaneyl)ethyl methacrylate, N-(2-(tritylthio) ethyl) acrylamide, a monomer including one or more boronic acid groups, a monomer containing one or more disulfide-forming groups, a halogenated versions of each of these, or a derivative of any one of these or copolymer of anyone of these, wherein the first type of mucin-binding unit is different than the second type of mucin-binding unit;

wherein the first type of mucin binding unit comprises 1 functional unit to about 5% of the first water-soluble polymer based on molecular weight; wherein the second type of mucin binding unit comprises 1 functional unit to about 5% of the first water-soluble polymer based on molecular weight.

2. The composition of claim 1, wherein the backbone unit comprises monomer units, copolymers including the monomer units, or both the monomer units and the copolymers, wherein the monomer unit is selected from the group consisting of: an acrylamide monomer, a methacrylamide monomer, an acrylate monomer, a methacrylate monomer, a styrenic monomer, a vinyl pyridine monomer, a maleimide monomer, a maleic anhydride-derived monomer, a vinyl ester monomer, a vinyl ether monomer, a vinyl amide monomer, a vinyl amine monomer, a vinyl halide monomer, or a derivative of anyone of these.

3. The composition of claim 1, wherein the backbone unit comprises a monomer unit, a copolymer including the monomer unit or both, wherein the monomer unit is selected from the group consisting of: acrylamide, N,N-dimethylacrylamide, N,N-dialkylacrylamides, N-alkylacrylamides, N,N-dialkyl methacrylamides, N-alkyl methacrylamides, poly(ethlylene glycol) acrylate, poly(ethylene glycol) methacrylate, poly(ethylene glycol) acrylamide, and poly(ethylene glycol) methacrylamide.

4. The composition of claim 1, wherein the backbone unit is N,N-dimethylacrylamide.

5. The composition of claim 1, wherein the first water-soluble polymer includes a second type of mucin-binding unit, wherein the second type of mucin-binding unit comprises monomer units, copolymers that include the monomer units, or both, wherein the monomer unit is selected from the group consisting of: acrylic acid, methacrylic acid, 4-vinylbenzoic acid, 4-(acrylamido)phenylboronic acid, 3-(acrylamido)phenylboronic acid, (2-(3-acrylamidopropanamido) phenyl) boronic acid (APAPBA), 2-(acrylamido) phenylboronic acid, 4-vinylphenylboronic acid, 3-vinylphenylboronic acid, 2-vinylphenylboronic acid, 2-(pyridin-2-yldisulfaneyl)ethyl methacrylate, pyridyl disulfide ethyl acrylate, pyridyl disulfide ethyl acrylamido, pyridyl disulfide alkyl (e.g. ethyl) methacrylamido, 2-(pyridin-2-yldisulfaneyl)ethyl acrylate, 2-(pyridin-2-yldisulfaneyl)ethyl acrylamido, 2-(pyridin-2-yldisulfaneyl)ethyl methacrylate, or 2-(pyridin-2-yldisulfaneyl)ethyl methacrylate, N-(2-(tritylthio)ethyl) acrylamide, a monomer including one or more boronic acid groups, a monomer containing one or more disulfide-forming groups, a halogenated versions of each of these, or a derivative of any one of these or copolymer of anyone of these, wherein the first type of mucin-binding unit is different than the second type of mucin-binding unit.

6. The composition of claim 5, wherein the first water-soluble polymer includes a third type of mucin-binding unit, wherein the third type of mucin-binding unit comprises monomer units, copolymers that include the monomer units, or both, wherein the monomer unit is selected from the group consisting of: acrylic acid, methacrylic acid, 4-vinylbenzoic acid, 4-(acrylamido)phenylboronic acid, 3-(acrylamido)phenylboronic acid, (2-(3-acrylamidopropanamido) phenyl) boronic acid (APAPBA), 2-(acrylamido) phenylboronic acid, 4-vinylphenylboronic acid, 3-vinylphenylboronic acid, 2-vinylphenylboronic acid, 2-(pyridin-2-yldisulfaneyl)ethyl methacrylate, pyridyl disulfide ethyl acrylate, pyridyl disulfide ethyl acrylamido, pyridyl disulfide alkyl (e.g. ethyl) methacrylamido, 2-(pyridin-2-yldisulfaneyl)ethyl acrylate, 2-(pyridin-2-yldisulfaneyl)ethyl acrylamido, 2-(pyridin-2-yldisulfaneyl)ethyl methacrylate, or 2-(pyridin-2-yldisulfaneyl)ethyl methacrylate, N-(2-(tritylthio)ethyl) acrylamide, a monomer including one or more boronic acid groups, a monomer containing one or more disulfide-forming groups, a halogenated versions of each of these, or a derivative of any one of these or copolymer of anyone of these, wherein the first type of mucin-binding unit is different than the second type of mucin-binding unit, wherein the second type of mucin-binding unit is different than the third type of mucin-binding unit monomer including one or more pyridyl disulfide groups, or a derivative of any one of these.

7. The composition of claim 6, wherein the first type of mucin binding unit comprises 1 functional unit to about 5% of the first water-soluble polymer based on molecular weight; wherein the second type of mucin binding unit comprises 1 functional unit to about 5% of the first water-soluble polymer based on molecular weight; wherein the third type of mucin binding unit comprises 1 functional unit to about 5% of the first water-soluble polymer based on molecular weight.

8. The composition of claim 1, wherein the first water-soluble polymer has a structure that is linear or non-linear, wherein the non-linear structure is selected from the group consisting of star-like, branched, hyperbranched, cyclic, graph copolymer, or bottle brush-like.

9. The composition of claim 1, wherein the first type of mucin binding unit is located solely at one or both terminal ends of the first water-soluble polymer.

10. The composition of claim 1, wherein the first water-soluble polymer is selected from the group consisting of: a block copolymer, a random copolymer, a statistical copolymer, an alternative copolymer, or a gradient copolymer.

11. The composition of claim 10, wherein the block copolymer is an AB diblock copolymer or an ABA triblock copolymer, optionally wherein the mucin-binding units are isolated on the A block of the AB diblock copolymer or A block of the ABA triblock copolymer.

12. The composition of claim 1, wherein the first water-soluble polymer has the following chemical structure:

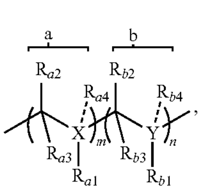

wherein unit a is the backbone unit and m is greater than 50% of the first water-soluble polymer based on molecular weight, wherein unit b is the first type of mucin binding unit and n is 1 unit to about 50% of the first water-soluble polymer based on molecular weight, wherein unit a and unit b are different from one another, $R_{a1}$, $R_{a2}$, $R_{a3}$, $R_{a4}$, $R_{b1}$, $R_{b2}$, $R_{b3}$, and $R_{b4}$, independently of one another, are selected from: H, —$OR_1$, —$NR_1R_2$, —$N^+(R_1)_3$, —$N^+(R_1)_2(R_2)$, —$N^+(R_1)$ $(R_2)(R_3)$, —$S(O)_2R_1$, —$S(O)_2OR_1$, —$S(O)_2NR_1R_2$, —$NR_1S(O)_2R_2$, —$NR_1C(O)R_2$, —$C(O)R_1$, —C(O) $OR_1$, —$C(O)NR_1R_2$, —$NR_1C(O)OR_2$, —$NR_1$C(O) $NR_1R_2$, —$OC(O)NR_1R_2$, —$NR_1S(O)_2NR_1R_2$, —C(O) $NR_1S(O)_2NR_1R_2$, catechol, a boronic acid group, and a pyridyl disulfide group, where each $R_1$, $R_2$, and $R_3$ is independently H or a linear or branched $C_{1-18}$ alkyl as well as —$C(O)OCH_2CH_2$—OH, —$C(O)OCH_2CH_2$—$N(CH_3)_2$, —$C(O)OCH_2CH_2$—$N^+(CH_3)_3$, —C(O) $OCH_2CH_2$—$OSO_3$—, —$C(O)OCH_2CH_2$—$OSO_3H$, —$C(O)OCH_2CH_2$—$SO_3$, —$C(O)OCH_2CH_2$—$SO_3H$, and —$C(O)N(H)C((CH_3)_2)CH_2SO_3$, —C(O)N(H)C $((CH_3)_2)CH_2SO_3H$, wherein one of $R_{b1}$, $R_{b2}$, $R_{b3}$, $R_{b4}$, is a boronic acid group, wherein X is C, and wherein Y is C.

13. The composition of claim 1, wherein the first water-soluble polymer has the following chemical structure:

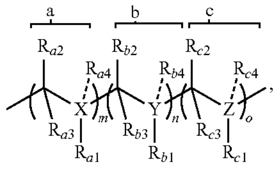

wherein unit a is the backbone unit and m is greater than 50% of the first water-soluble polymer based on molecular weight, wherein unit b is the first type of mucin binding unit and n is 1 unit to about 50% of the first water-soluble polymer based on molecular weight, wherein unit c is the second type of mucin binding unit and o is 1 unit to about 50% of the first water-soluble polymer based on molecular weight, wherein unit a and unit b are different from one another, $R_{a1}$, $R_{a2}$, $R_{a3}$, $R_{a4}$, $R_{b1}$, $R_{b2}$, $R_{b3}$, $R_{b4}$, $R_{c1}$, $R_{c2}$, $R_{c3}$, and $R_{c4}$, independently of one another, can be H, —$OR_1$, —$NR_1R_2$, —$N^+(R_1)_3$, —$N^+(R_1)_2(R_2)$, —$N^+(R_1)(R_2)$ $(R_3)$, —$S(O)_2R_1$, —$S(O)_2OR_1$, —$S(O)_2NR_1R_2$, —$NR_1S(O)_2R_2$, —$NR_1C(O)R_2$, —$C(O)R_1$, —C(O) $OR_1$, —$C(O)NR_1R_2$, —$NR_1C(O)OR_2$, —$NR_1$C(O) $NR_1R_2$, —$OC(O)NR_1R_2$, —$NR_1S(O)_2NR_1R_2$, —C(O) $NR_1S(O)_2NR_1R_2$, catechol, a boronic acid group, and a pyridyl disulfide group, where each $R_1$, $R_2$, and $R_3$ is independently H or linear or branched $C_{1-18}$ alkyl as well as —$C(O)OCH_2CH_2$—OH, —$C(O)OCH_2CH_2$—$N(CH_3)_2$, —$C(O)OCH_2CH_2$—$N^+(CH_3)_3$, —C(O) $OCH_2CH_2$—$OSO_3$—, —$C(O)OCH_2CH_2$—$OSO_3H$, —$C(O)OCH_2CH_2$—$SO_3$—, —$C(O)OCH_2CH_2$—$SO_3H$, and —$C(O)N(H)C((CH_3)_2)$ $CH_2SO_3$—, —C(O) $N(H)C((CH_3)_2)$ $CH_2SO_3H$, wherein one of $R_{b1}$, $R_{b2}$, $R_{b3}$, $R_{b4}$, is a boronic acid group, wherein X is C, wherein Y is C, and wherein Z is C.

14. The composition of claim 13, wherein unit a, unit b, and unit c are different from one another.

15. The composition of claim 1, wherein the first water-soluble polymer has chemical structure as shown below:

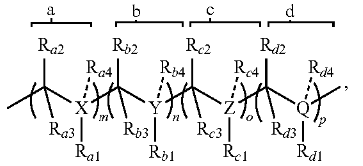

wherein unit a is the backbone unit and m is greater than 50% of the first water-soluble polymer based on molecular weight, wherein unit b is the first type of mucin binding unit and n is 1 unit to about 50% of the first water-soluble polymer based on molecular weight, wherein unit c is the second type of mucin binding unit and o is 1 unit to about 50% of the first water-soluble polymer based on molecular weight, wherein unit d is the second type of mucin binding unit and o is 1 unit to about 50% of the first water-soluble polymer based on molecular weight, wherein unit a and unit b are different from one another, $R_{a1}$, $R_{a2}$, $R_{a3}$, $R_{a4}$, $R_{b1}$, $R_{b2}$, $R_{b3}$, $R_{b4}$, $R_{c1}$, $R_{c2}$, $R_{c3}$, $R_{c4}$, $R_{d1}$, $R_{d2}$, $R_{d3}$, and $R_{d4}$, independently of one another, can be H, —$OR_1$, —$NR_1R_2$, —$N^+(R_1)_3$, —$N^+(R_1)_2$ $(R_2)$, —$N^+(R_1)$ $(R_2)$ $(R_3)$, —$S(O)_2R_1$, —$S(O)_2OR_1$, —$S(O)_2NR_1R_2$, —$NR_1S(O)_2R_2$, —$NR_1C(O)R_2$, —$C(O)R_1$, —$C(O)OR_1$, —$C(O)NR_1R_2$, —$NR_1$C(O) $OR_2$, —$NR_1C(O)NR_1R_2$, —$OC(O)NR_1R_2$, —$NR_1$S $(O)_2NR_1R_2$, —$C(O)NR_1S(O)_2NR_1R_2$, catechol, a boronic acid group, and a pyridyl disulfide group, where each $R_1$, $R_2$, and $R_3$ is independently H or linear or branched $C_{1-18}$ alkyl as well as —$C(O)OCH_2CH_2$—OH, —$C(O)OCH_2CH_2$—$N(CH_3)_2$, —C(O) $OCH_2CH_2$—$N^+(CH_3)_3$, —$C(O)OCH_2CH_2$—$OSO_3$—, —$C(O)OCH_2CH_2$—$OSO_3H$, —$C(O)OCH_2CH_2$—$SO_3$—, —$C(O)OCH_2CH_2$—$SO_3H$, and —C(O)N(H)C $((CH_3)_2)$ $CH_2SO_3$, —$C(O)N(H)C((CH_3)_2)$ $CH_2SO_3H$, wherein one of $R_{b1}$, $R_{b2}$, $R_{b3}$, $R_{b4}$, is a boronic acid group, wherein X is C, wherein Y is C, wherein Z is C, and wherein Q is C.

16. The composition of claim 15, wherein unit a, unit b, unit c, and unit d are different from one another.

17. A synthetic method of making the first water-soluble polymer of claim 1, comprising: polymerizing a backbone unit and at least one mucin-binding unit to form the first water-soluble polymer of claim 1.

18. A composition comprising: an ophthalmic aqueous solution including a first water-soluble polymer, wherein the first water-soluble polymer includes a plurality of backbone units and at least one first type of a mucin-binding unit, wherein the backbone units comprise greater than 50% of the first water-soluble polymer based on molecular weight, wherein the first type of mucin-binding unit comprises of 1 unit up to 50% of the first water-soluble polymer based on molecular weight, wherein the first type of mucin-binding unit comprises monomer units, copolymers that include the monomer units, or both, wherein the monomer unit includes a boronic acid group, wherein the first type of mucin binding unit is located solely at one or both terminal ends of the first water-soluble polymer.

19. The composition of claim 18, wherein the backbone unit comprises monomer units, copolymers including the monomer units, or both the monomer units and the copolymers, wherein the monomer unit is selected from the group consisting of: an acrylamide monomer, a methacrylamide monomer, an acrylate monomer, a methacrylate monomer, a styrenic monomer, a vinyl pyridine monomer, a maleimide monomer, a maleic anhydride-derived monomer, a vinyl ester monomer, a vinyl ether monomer, a vinyl amide monomer, a vinyl amine monomer, a vinyl halide monomer, or a derivative of anyone of these.

20. The composition of claim 18, wherein the backbone unit comprises a monomer unit, a copolymer including the monomer unit or both, wherein the monomer unit is selected from the group consisting of: acrylamide, N,N-dimethylacrylamide, N,N-dialkylacrylamides, N-alkylacrylamides, N,N-dialkyl methacrylamides, N-alkyl methacrylamides, poly(ethlylene glycol) acrylate, poly(ethylene glycol) methacrylate, poly(ethylene glycol) acrylamide, and poly(ethylene glycol) methacrylamide.

21. The composition of claim 18, wherein the backbone unit is N,N-dimethylacrylamide.

22. The composition of claim 18, wherein the first water-soluble polymer has the following chemical structure:

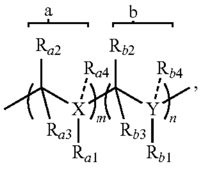

wherein unit a is the backbone unit and m is greater than 50% of the first water-soluble polymer based on molecular weight, wherein unit b is the first type of mucin binding unit and n is 1 unit to about 50% of the first water-soluble polymer based on molecular weight, wherein unit a and unit b are different from one another, $R_{a1}$, $R_{a2}$, $R_{a3}$, $R_{a4}$, $R_{b1}$, $R_{b2}$, $R_{b3}$, and $R_{b4}$, independently of one another, are selected from: H, —$OR_1$, —$NR_1R_2$, —$N^+(R_1)_3$, —$N^+(R_1)_2(R_2)$, —$N^+(R_1)$ $(R_2)$ $(R_3)$, —$S(O)_2R_1$, —$S(O)_2OR_1$, —$S(O)_2NR_1R_2$, —$NR_1S(O)_2R_2$, —$NR_1C(O)R_2$, —$C(O)R_1$, —$C(O)OR_1$, —$C(O)NR_1R_2$, —$NR_1C(O)OR_2$, —$NR_1C(O)NR_1R_2$, —$OC(O)NR_1R_2$, —$NR_1S(O)_2NR_1R_2$, —$C(O)NR_1S(O)_2NR_1R_2$, catechol, a boronic acid group, and a pyridyl disulfide group, where each $R_1$, $R_2$, and $R_3$ is independently H or a linear or branched $C_{1-18}$ alkyl as well as —$C(O)OCH_2CH_2$—OH, —$C(O)OCH_2CH_2$—$N(CH_3)_2$, —$C(O)OCH_2CH_2$—$N^+(CH_3)_3$, —$C(O)OCH_2CH_2$—$OSO_3$—, —$C(O)OCH_2CH_2$—$OSO_3H$, —$C(O)OCH_2CH_2$—$SO_3$—, —$C(O)OCH_2CH_2$—$SO_3H$, and —$C(O)N(H)C((CH_3)_2)$ $CH_2SO_3$—, —$C(O)N(H)C((CH_3)_2)$ $CH_2SO_3H$, wherein one of $R_{b1}$, $R_{b2}$, $R_{b3}$, $R_{b4}$, is a boronic acid group, wherein X is C, and wherein Y is C.

23. The composition of claim 18, wherein the first water-soluble polymer has the following chemical structure:

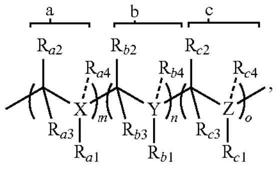

wherein unit a is the backbone unit and m is greater than 50% of the first water-soluble polymer based on molecular weight, wherein unit b is the first type of mucin binding unit and n is 1 unit to about 50% of the first water-soluble polymer based on molecular weight, wherein unit c is the second type of mucin binding unit and o is 1 unit to about 50% of the first water-soluble polymer based on molecular weight, wherein unit a and unit b are different from one another, $R_{a1}$, $R_{a2}$, $R_{a3}$, $R_{a4}$, $R_{b1}$, $R_{b2}$, $R_{b3}$, $R_{b4}$, $R_{c1}$, $R_{c2}$, $R_{c3}$, and $R_{c4}$, independently of one another, can be H, —$OR_1$, —$NR_1R_2$, —$N^+(R_1)_3$, —$N^+(R_1)_2(R_2)$, —$N^+(R_1)$ $(R_2)$ $(R_3)$, —$S(O)_2R_1$, —$S(O)_2OR_1$, —$S(O)_2NR_1R_2$, —$NR_1S(O)_2R_2$, —$NR_1C(O)R_2$, —$C(O)R_1$, —$C(O)OR_1$, —$C(O)NR_1R_2$, —$NR_1C(O)OR_2$, —$NR_1C(O)NR_1R_2$, —$OC(O)NR_1R_2$, —$NR_1S(O)_2NR_1R_2$, —$C(O)NR_1S(O)_2NR_1R_2$, catechol, a boronic acid group, and a pyridyl disulfide group, where each $R_1$, $R_2$, and $R_3$ is independently H or linear or branched $C_{1-18}$ alkyl as well as —$C(O)OCH_2CH_2$—OH, —$C(O)OCH_2CH_2$—$N(CH_3)_2$, —$C(O)OCH_2CH_2$—$N^+(CH_3)_3$, —$C(O)OCH_2CH_2$—$OSO_3$—, —$C(O)OCH_2CH_2$—$OSO_3H$, —$C(O)OCH_2CH_2$—$SO_3$, —$C(O)OCH_2CH_2$—$SO_3H$, and —$C(O)N(H)C((CH_3)_2)$ $CH_2SO_3$—, —$C(O)N(H)C((CH_3)_2)$ $CH_2SO_3H$, wherein one of $R_{b1}$, $R_{b2}$, $R_{b3}$, $R_{b4}$, is a boronic acid group, wherein X is C, wherein Y is C, and wherein Z is C.

24. The composition of claim 23, wherein unit a, unit b, and unit c are different from one another.

25. The composition of claim 18, wherein the first water-soluble polymer has chemical structure as shown below:

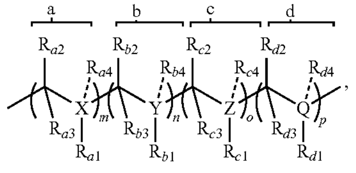

wherein unit a is the backbone unit and m is greater than 50% of the first water-soluble polymer based on molecular weight, wherein unit b is the first type of mucin binding unit and n is 1 unit to about 50% of the first water-soluble polymer based on molecular weight, wherein unit c is the second type of mucin binding unit and o is 1 unit to about 50% of the first water-soluble polymer based on molecular weight, wherein unit d is the second type of mucin binding unit and o is 1 unit to about 50% of the first water-soluble polymer based on molecular weight, wherein unit a and unit b are different from one another, $R_{a1}$, $R_{a2}$, $R_{a3}$, $R_{a4}$, $R_{b1}$, $R_{b2}$, $R_{b3}$, $R_{b4}$, $R_{c1}$, $R_{c2}$, $R_{c3}$, $R_{c4}$, $R_{d1}$, $R_{a2}$, $R_{a3}$, and $R_{d4}$, independently of one another, can be H, $—OR_1$, $—NR_1R_2$, $—N^+(R_1)_3$, $—N^+(R_1)_2(R_2)$, $—N^+(R_1)(R_2)(R_3)$, $—S(O)_2R_1$, $—S(O)_2OR_1$, $—S(O)_2NR_1R_2$, $—NR_1S(O)_2R_2$, $—NR_1C(O)R_2$, $—C(O)R_1$, $—C(O)OR_1$, $—C(O)NR_1R_2$, $—NR_1C(O)OR_2$, $—NR_1C(O)NR_1R_2$, $—OC(O)NR_1R_2$, $—NR_1S(O)_2NR_1R_2$, $—C(O)NR_1S(O)_2NR_1R_2$, catechol, a boronic acid group, and a pyridyl disulfide group, where each $R_1$, $R_2$, and $R_3$ is independently H or linear or branched $C_{1-18}$ alkyl as well as $—C(O)OCH_2CH_2—OH$, $—C(O)OCH_2CH_2—N(CH_3)_2$, $—C(O)OCH_2CH_2—N^+(CH_3)_3$, $—C(O)OCH_2CH_2—OSO_3—$, $—C(O)OCH_2CH_2—OSO_3H$, $—C(O)OCH_2CH_2—SO_3—$, $—C(O)OCH_2CH_2—SO_3H$, and $—C(O)N(H)C((CH_3)_2)CH_2SO_3$, $—C(O)N(H)C((CH_3)_2)CH_2SO_3H$, wherein one of $R_{b1}$, $R_{b2}$, $R_{b3}$, $R_{b4}$, is a boronic acid group, wherein X is C, wherein Y is C, wherein Z is C, and wherein Q is C.

26. The composition of claim 25, wherein unit a, unit b, unit c, and unit d are different from one another.

* * * * *